United States Patent [19]

Lu

[11] Patent Number: 5,395,358
[45] Date of Patent: Mar. 7, 1995

[54] WETTING INDICATOR FOR A DIAPER

[76] Inventor: Chin B. Lu, P.O. Box 82-144, Taipei, Taiwan, Prov. of China

[21] Appl. No.: 183,973

[22] Filed: Jan. 21, 1994

[51] Int. Cl.6 .......................................... A61F 13/15
[52] U.S. Cl. ................................... 604/361; 340/604; 340/573
[58] Field of Search ............................ 604/359–361; 128/886; 340/604, 573

[56] References Cited

U.S. PATENT DOCUMENTS

| | | | |
|---|---|---|---|
| 4,205,672 | 6/1980 | Dvorak | 604/361 |
| 4,484,573 | 11/1984 | Yoo | 128/866 |
| 4,768,023 | 8/1988 | Xie | 340/573 |
| 4,796,014 | 1/1989 | Chia | 604/361 |
| 5,264,830 | 11/1993 | Kline et al. | 604/361 |
| 5,266,928 | 11/1993 | Johnson | 340/604 |

*Primary Examiner*—Randall L. Green
*Assistant Examiner*—Rob Clarke
*Attorney, Agent, or Firm*—Alfred Lei

[57] ABSTRACT

A wetting indicator for a diaper including a seat having an inclined surface and a slot, a sensor provided with a head portion and a blade portion extending from said head portion, a positive contact member disposed within said blade portion and being in communication with the perforations of said blade portion, a negative contact member disposed with said blade portion and being in communication with the perforations of said blade portion, a battery disposed within said head portion and having a positive electrode and a negative electrode, the positive electrode being connected with said positive contact member, and a music IC disposed within said head portion and electrically connected with the positive electrode of said battery and said negative contact member.

2 Claims, 4 Drawing Sheets

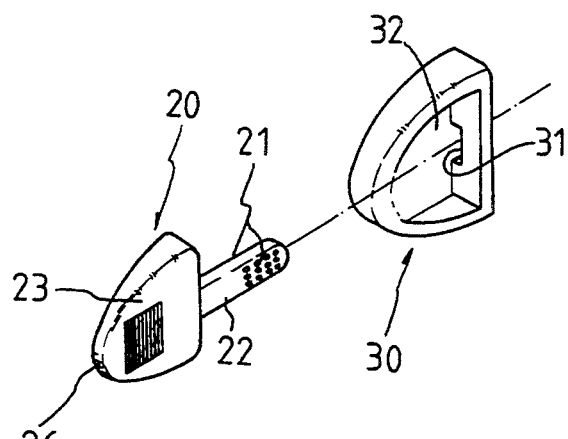
F I G. 1
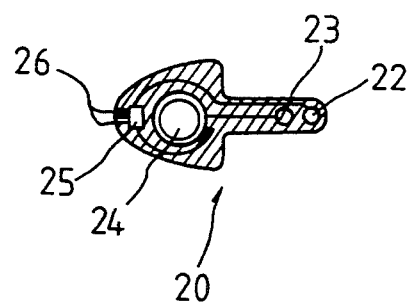
F I G. 2
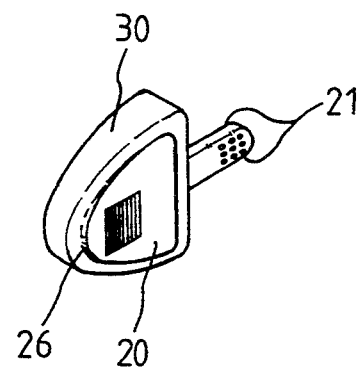
F I G. 3

WETTING INDICATOR FOR A DIAPER

BACKGROUND OF THE INVENTION

Heretofore, a diaper which will display a pattern when made wet by a child has been developed to arouse the attention of the parent. However, such a diaper still has the following drawbacks:

1. The pattern cannot be repeatedly used.
2. The parent will not observe the pattern unless they look at it.
3. The diaper will not do much help to prevent skin disease.

Therefore, it is an object of the present invention to provide a wetting indicator for a diaper which may obviate and mitigate the above-mentioned drawbacks.

SUMMARY OF THE INVENTION

This invention relates to a wetting indicator for a diaper.

It is the primary object of the present invention to provide a wetting indicator for a diaper which will produce music when the child makes the diaper wet.

It is another object of the present invention to provide a wetting indicator for a diaper which can be repeatedly used.

It is still another object of the present invention to provide a wetting indicator for a diaper which is convenient to use.

It is still another object of the present invention to provide a wetting indicator for a diaper which is fit for practical use.

It is a further object of the present invention to provide a wetting indicator for a diaper which is facile to manufacture.

These and other objects and advantages of the present invention will become clear to those skilled in the art in view of the description of the best presently known mode of carrying out the invention and the industrial applicability of the preferred embodiment, as described herein and as illustrated in the several figures of the drawing.

BRIEF DESCRIPTION OF THE DRAWINGS

FIG. 1 is an exploded view of the present invention;
FIG. 2 is a sectional view of the present invention;
FIG. 3 is a perspective view of the present invention.

DETAILED DESCRIPTION OF THE PREFERRED EMBODIMENT

Figure 4:
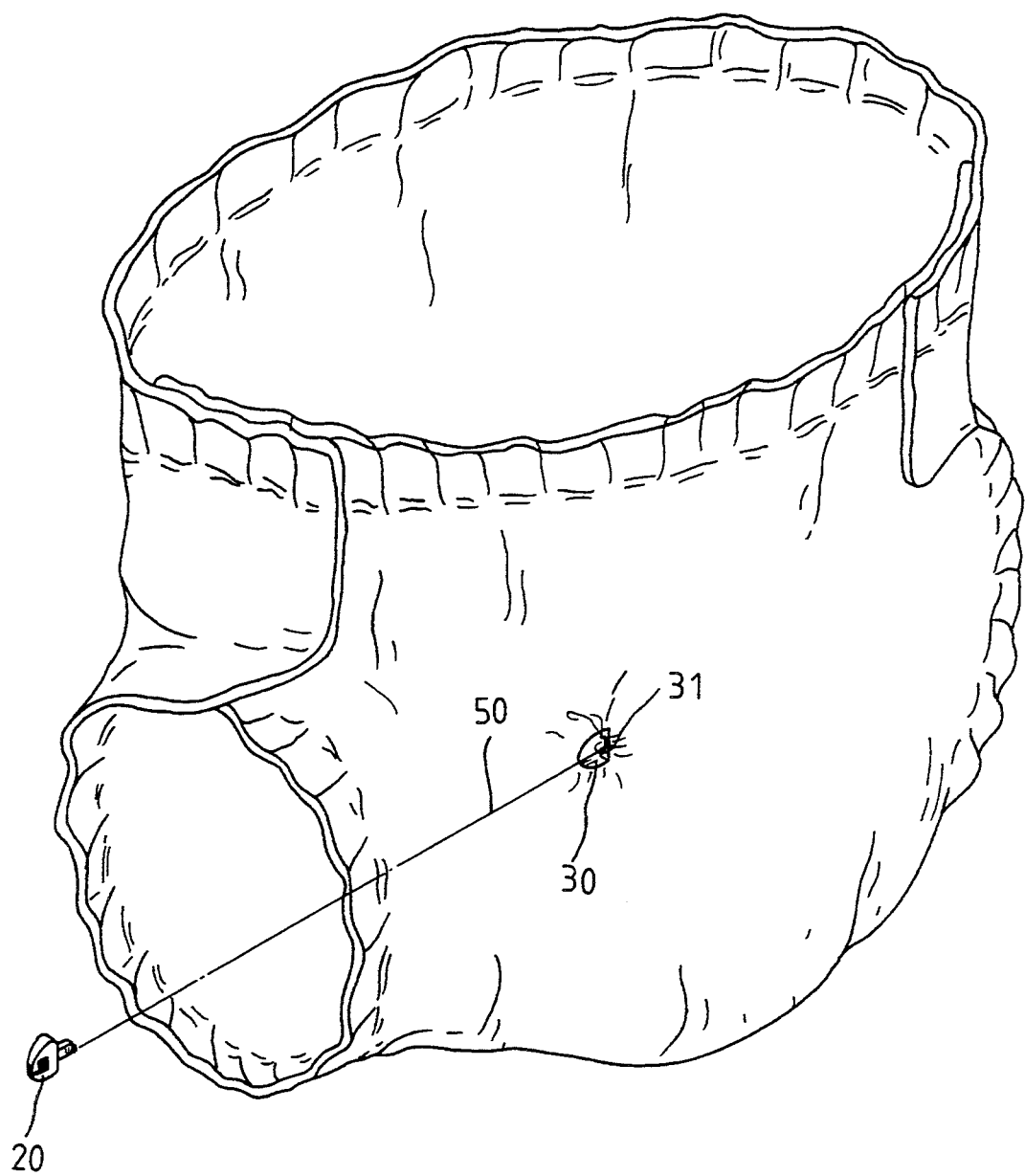
FIG. 4 shows an application of the present invention.

For purpose of promoting an understanding of the principles of the invention, reference will now be made to the embodiment illustrated in the drawings. Specific language will be used to describe same. It will, nevertheless, be understood that no limitation of the scope of the invention is thereby intended, such alternations and further modifications in the illustrated device, and such further applications of the principles of the invention as illustrated herein being contemplated as would normally occur to one skilled in the art to which the invention relates.

With reference to the drawings and in particular to FIG. 1 thereof, the wetting indicator for a diaper comprises a seat 30 and a sensor 20. The seat 30 is an integral member having an inclined surface 32 and a slot 31. The sensor 20 is provided with a head portion 23 and a blade portion 22 extending from the head portion 23. The head portion 23 has a sound emitting outlet 26 while the blade portion 22 is provided with a plurality of perforations 21.

As shown in FIGS. 2 and 3, there are a positive contact member 61 and a negative contact member 62 disposed within interior of the blade portion, 22 and being in communication with the perforations 21. Further, the head portion 23 is provided with a battery 24 and a music IC 25 in its interior. The positive contact member 61 and the negative contact member 62 are respectively connected with the positive electrode of the battery 24 and the music IC 25. The music IC 25 is further connected to the negative electrode of the battery 24.

When the sensor 20 is flooded with urine, the urine will flow into the perforations 21 thereby electrically connecting the positive contact member 61 with the negative contact member 62 and therefore, forming a closed circuit. In the meantime, the music IC will produce music through the sound emitting outlet 26 of the head portion 23.

It should be noted that the seat 30 is embedded into the diaper in advance so that the seat 30 lies on a predetermined urine saturation line 50 (see FIG. 4) of the diaper. When in use, the head portion 20 is inserted into the seat 30. As the child has urinated, the music IC 25 will produce music, arousing the attention of his parents. Then, the head portion 20 is removed from the seat 30 and inserted into the seat 30 of another diaper so that the blade portion 22 of the sensor 20 will be dried by the diaper and restore its function.

Figure 5A:
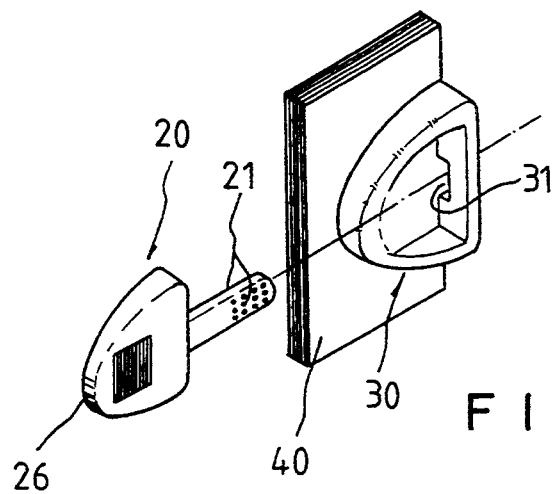
FIG. 5A shows a second preferred embodiment of the present invention.
Figure 5B:
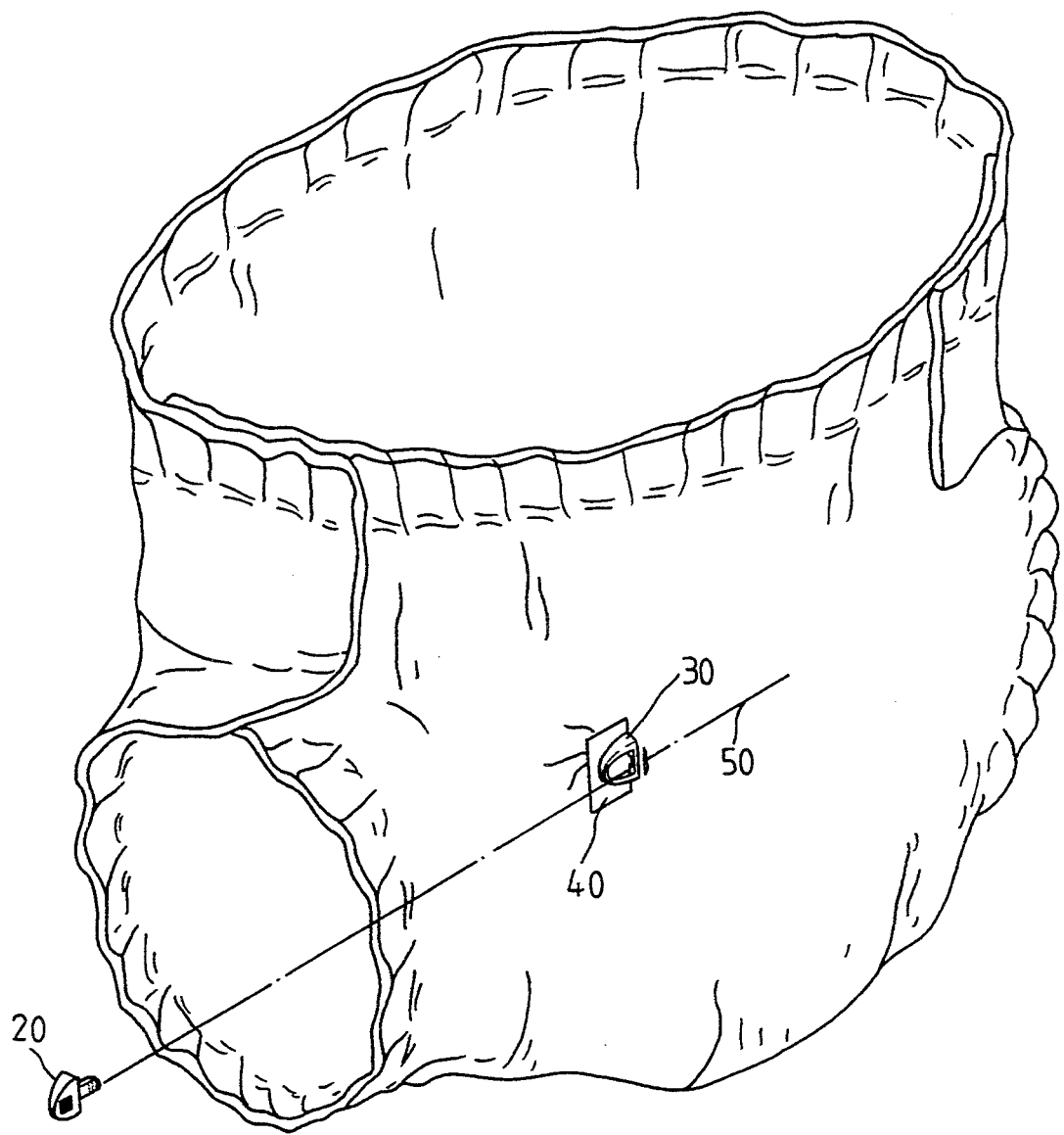
FIG. 5B shows an application of the second preferred embodiment of the present invention.

FIGS. 5A and 5B show a second preferred embodiment of the present invention. As illustrated, the back side of the seat 30 is provided with an adhesive pad 40 so that the present invention can be conveniently applied to all kinds of diapers.

Figure 6A:
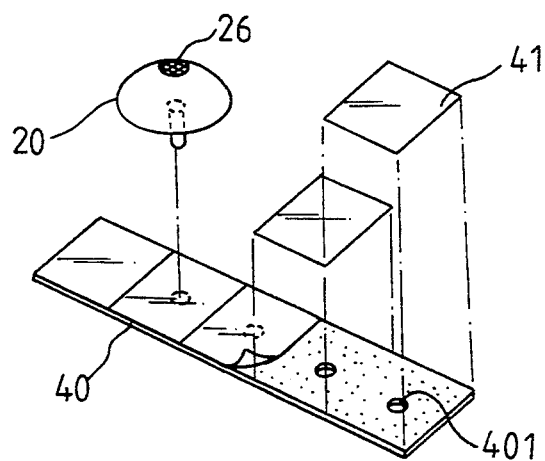
FIG. 6A shows a third preferred embodiment of the present invention.
Figure 6B:
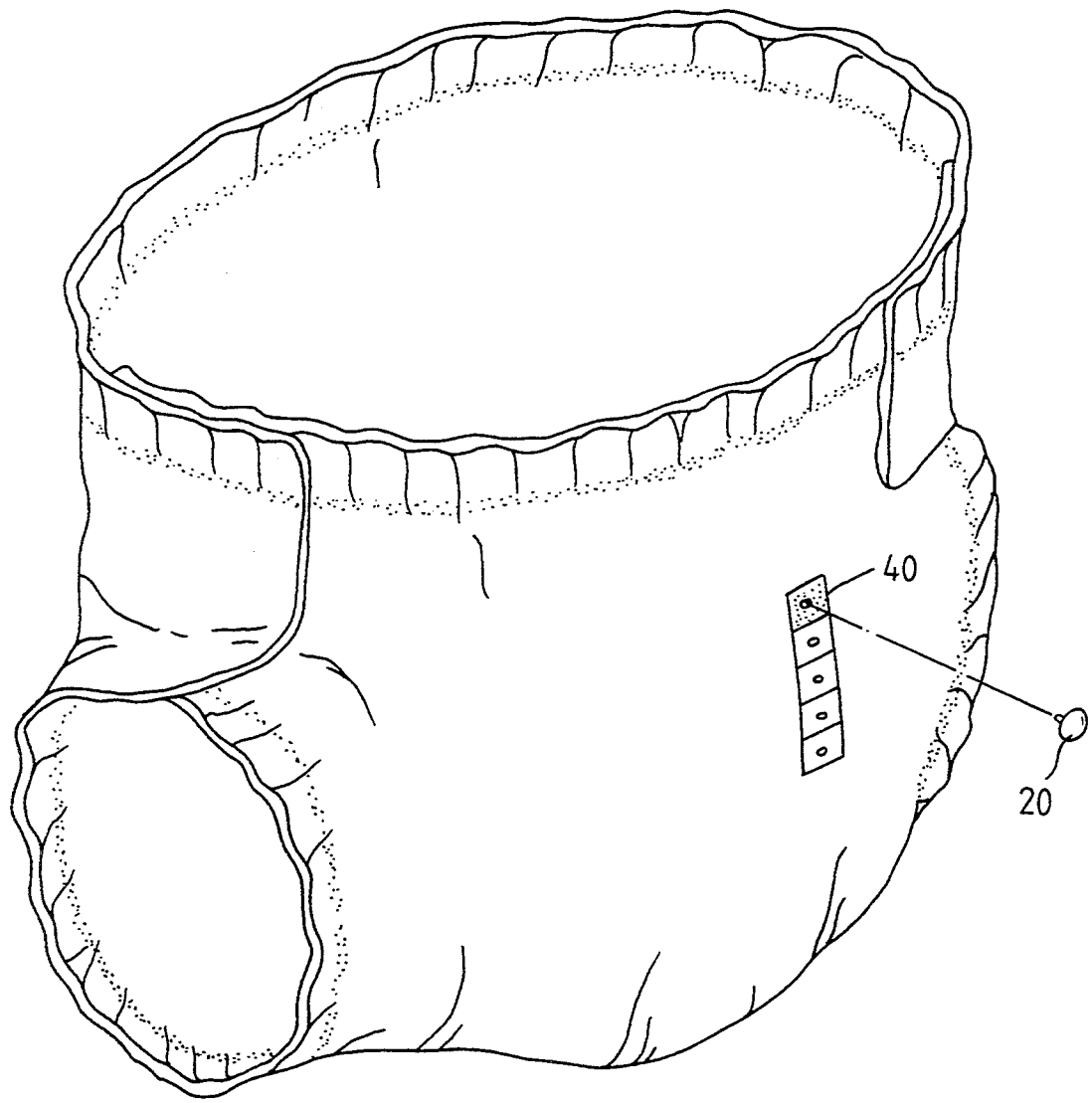
FIG. 6B shows an application of the third preferred embodiment of the present invention.

FIGS. 6A and 6B show a third preferred embodiment of the present invention. As may be seen, the seat 30 is replaced with a strip of adhesive pad 40 provided with a plurality of holes 401 and five pieces of paper 41 on the top and so the sensor 20 may be selectively engaged with one of the holes 401 as desired.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

I claim:

1. A wetting indicator for a diaper comprising:
   a seat having an inclined surface and a slot;
   a sensor provided with a head portion and a blade portion extending from said head portion, said blade portion being provided with a plurality of perforations and adapted to engage with the slot of said seat, said head portion having a sound emitting outlet;

a positive contact member disposed within said blade portion and being in communication with the perforations of said blade portion;

a negative contact member disposed with said blade portion and being in communication with the perforations of said blade portion;

a battery disposed within said head portion and having a positive electrode and a negative electrode, the positive electrode being connected with said positive contact member; and a music IC disposed Within said head portion and electrically connected with the positive electrode of said battery and said negative contact member.

2. The wetting indicator for a diaper as claimed in claim 1, wherein said seat is provided with an adhesive pad at the back.

* * * * *